United States Patent [19]

Grossman et al.

[11] Patent Number: 5,554,507
[45] Date of Patent: Sep. 10, 1996

[54] BACILLUS SUBTILIS SIDEROPHORE GENES

[75] Inventors: Trudy H. Grossman, Mount Kisco, N.Y.; Marcia S. Osburne, Lexington, Mass.

[73] Assignee: American Cyanamid Company, Wayne, N.J.

[21] Appl. No.: 51,142

[22] Filed: Apr. 22, 1993

Related U.S. Application Data

[63] Continuation-in-part of Ser. No. 922,602, Jul. 30, 1992, abandoned.

[51] Int. Cl.$^6$ ............................. C12N 1/21; C12N 5/10; C12N 15/63; C12Q 1/18
[52] U.S. Cl. .................. 435/32; 435/240.2; 435/252.3; 435/252.33; 435/254.11; 435/320.1
[58] Field of Search .................... 536/23.2, 23.7; 435/320.1, 252.3, 240.2, 252.33, 29, 32

[56] References Cited

U.S. PATENT DOCUMENTS

| | | | |
|---|---|---|---|
| 4,540,667 | 9/1985 | Orser et al. | 435/172.3 |
| 5,070,020 | 12/1991 | Ingolia et al. | 435/183 |
| 5,079,143 | 1/1992 | Klein et al. | 435/29 |

OTHER PUBLICATIONS

Ames, G. F. L., S.S. Mimura and V. Shyamala, TEMS Microbiol. Rev. 75:429–446, 1990.
Armstrong, S. K., G. S. Pettis, L. J. Forrester and M. A. McIntosh, Mol. Microbiol., 3:757–766, 1989.
DeLorenzo, V., S. Wee, M. Herrero, J. B. Neilands., J. Bacteriol., 169:2624–2630, 1987.
Earhart, C. F., in G. Winkelmann, D. van der Helm, J. B. Neilands (eds.), *Iron Transport in Microbes, Plants and Animals,* VCH Verlagsgesellschaft mbH. Weinheim, FRG, pp. 67–84, 1987.
Fleming, T. P., M. S. Nahlik, J. B. Neilands and M. A. McIntosh, Gene, 34:47–54, 1985.
Greenwood, K. T. and R. K. J. Luke, Biochem. Biophys. Acta., 614:185–195, 1980.
Ito, T. and J. B. Neilands, J. Am. Chem. Soc., 80:4645–4647, 1958.
Kratzschmar, J., M. Krause, and M. A. Marahiel, J. Bacteriol., 171:5922–5429, 1989.
Lankford, C.E., CRC Crit. Rev. Microbiol., 2:273–331, 1973.
Sawbrook, J., Fritsch, and T. Maniatis, Molecular Cloning: a Laboratory Manual (Table of Contents), Cold Spring Harbor Laboratory, 1989.
Miller, J. H., Experiments in Molecular Genetics (Table of Contents), Cold Spring Harbor Laboratory, 1972.
Nahlik, M. S., T. J. Brickman, B. A. Ozenberger, and M. A. McIntosh, J. Bacteriol. 171:784–790, 1989.
Nakano, M. M., R. Magnuson, A. Myers, J. Curry, A. D. Grossman and P. Zuber, J. Bacertiol., 173:1170–1178, 1991.
Neilands, J. B., Structure and Bonding, 58:1–24, 1984.
Ozenberger, B. A., T. J. Brickman and M. A. McIntosh, J. Bacteriol., 171:775–783, 1989.
Payne, S., CRC Crit. Rev. Microbiol., 16:81–111, 1988.
Schwyn, B. and J. B. Neilands, Anal. Biochem., 160:47–56, 1987.
Sonenshein, A. L., B. Cami, J. Brevet, and R. Cole, J. Bacteriol., 120:253–265, 1974.

(List continued on next page.)

*Primary Examiner*—Robert A. Wax
*Assistant Examiner*—Eric Grimes
*Attorney, Agent, or Firm*—Elizabeth M. Barnhard; Karen A. Lowney

[57] ABSTRACT

An isolated nucleic acid sequence is described having at least one siderophore biosynthetic gene from Bacillus subtilis encoding enzymes homologous to enterobactin enzymes EntA, EntB, EntC, EntE, and combinations thereof. Vectors containing the isolated nucleic acid sequence, host cells transformed wth the isolated nucleic acid sequence, and a method for identifying compounds having antibiotic activity against microorganisms with an enterobactin-type siderophore are also described.

12 Claims, 10 Drawing Sheets

OTHER PUBLICATIONS

Staab, J. F. and C. F. Earhart, J. Bacteriol., 172:6403–6410, 1990.
Takahashi, I., J. Gen. Microbiol., 31:211–217, 1963.
Tuckman, M. and M. S. Osburne, J. Bacteriol., 174:320–323, 1992.
Walker, J. E., M. Saraste, M. J. Runswick, N. J. Gay, EMBO J, 1:945–957, 1982.
Walsh, C. T., J. Liu, F. Rusnak, and M. Sakaitani, Chem., Rev., 90:1105–1129, 1990.
Way, J. C., M. A. Davis D. Morisato, D. E. Roberts and N. Kleckner, Gene, 32:369–379, 1984.
Schupp et al., Gene 64:179–188 (1988).
Singleton et al., *Dictionary of Microbiology and Molecular Biology,* 2nd Edition, John Wiley & Sons, New York, 1988, p. 850.
Nakano et al., Mol. Gen. Genet. 232:313–321 (1992).
Nikaido et al., in *Escherichia coli and Salmonella Typhimurium,* Neidhardt (ed.), Amer. Soc. Microbiol., Washington, DC, 1987 pp. 7–13.

```
                                                        C                              GCGCT
  1  TATTTTGCGTTTTTCATTGCCCCAGTCAATCCAGTTGCTGAATTATGCTGTGGCAAGGCGGACA CGA G

C
 69  TGAAAGCATCTCCGCCTGTACACTAAAAACAAAG CGCCTTGGCTTTGTTTTTTTATTTTCTCCTCTATA

CG
137  TGAGTCTTGTGGAAGTATGATAGGATGGTTTTGACAATCTTTTGCAGA GC GAGGATCTAGAATGAAGA
                                                                    M  K  I

205  TTTACGGAATTTATATGGACCGCCCCGCTTTCACAGGAAGAAAATGAACGGTTCATGTCTTTCATATCA
      Y  G  I  Y  M  D  R  P  L  S  Q  E  E  N  E  R  F  M  S  F  I  S

273  CCTGAAAAACGGGAGAAATGCCGGAGATTTTATCATAAAGAAGATGCTCACCGCACCCTGCTGGGAGA
      P  E  K  R  E  K  C  R  R  F  Y  H  K  E  D  A  H  R  T  L  L  G  D

341  TGTGCTCGTTCGCTCAGTCATAAGCAGGCAGTATCAGTTGGACAAATCCGATATCCGCTTTAGCACGC
      V  L  V  R  S  V  I  S  R  Q  Y  Q  L  D  K  S  D  I  R  F  S  T  Q

409  AGGAATACGGGAAGCCGTGCATCCCTGATCTTCCCGACGCTCATTTCAACATTTCTCACTCCGGACGC
      E  Y  G  K  P  C  I  P  D  L  P  D  A  H  F  N  I  S  H  S  G  R

477  TGGGTCATTTGCGCGTTTGATTCACAGCCGATCGGCATAGATATCGAAAAAACGAAACCGATCAGCCT
      W  V  I  C  A  F  D  S  Q  P  I  G  I  D  I  E  K  T  K  P  I  S  L

545  TGAGATCGCCAAGCGCTTCTTTTCAAAAACAGAGTACAGCGACCTTTTAGCAAAAGACAAGGACGAGC
      E  I  A  K  R  F  F  S  K  T  E  Y  S  D  L  L  A  K  D  K  D  E  Q
```

FIG.6A

```
                                        C
613  AGACAGACTATTTTTATCATCTATGGTCAATGAAAGAAAGCTTTATCAAACAAGGAAGGCAAAGGCTT
      T  D  Y  F  Y  H  L  W  S  M  K  E  S  F  I  K  Q  G  R  Q  R  L

681  ATCGCTTCCGCTTGATTCCTTTTCAGTGCGCCTGCA|CAGGACGGACAAGTATCCATTGAGCTTCCGGA
      I  A  S  A  *

749  CAGCCATTCCCCATGCTATATCAAAACGTATGAGGTCGATCCCGGCTACAAAATGGCTGTATGCGCCG

817  TACACCCTGATTTCCCCGAGGATATCACAATGGTCTCGTACGAAGAGCTTTTATAAATGGCTCATCAA

T
885  CAGCTTGACACCGCGCTCAATATCTTCCGTTTTCACATTGGAAATATTGATTTTTAATAGATTTTCTT

T                                        TC         T
953  TCGGATAATCTGATAAATAATGACGGTCTATCGCCTCAAGGAGAACCCCTTGTTTTTCCAGTCTATGA

△                                                              A
1021 AGTACACTCTTGAGGCGGGCAGATCCTGAGGAAGCACCAGATGGGTGTGCATACAGGGTGCCTGCCCG

T   T
1089 CTGGAGAACGTAAAGCGTCCGCTTCCCAGCTGCCTGTGAGTTCGAATGGCTTGATGTAGCCTCAGCGA

1157 CCGCTCTTTATAAGAATCTCTGATTTTCTCCTTATGCCTGCCGTACATACCGCTTTTCAGGTAAATCT
```

FIG.6B

```
                                                   T         A       T
1225  CCAATGCCGCTTGAGAAATCATCGAACAGTCGATGTCGTTCAGCTTTTTGTACGCATAGAACGTGTCA

A G C   G ACATCA
1293  GTCAGCGCTTCGGGCAAAACAGCCGCCCCCACGCGAGGCCGGGGAACATCATTTTCGAGAAGCTTTTC

1361  AAATAGATGACATGTGAGGACAGATCATATGCGTACAGCG
```

FIG.6C

```
                         1                                              49
E. coli EntD     MVDMKTTHTSLPFA.GHTLHEVEEDPANFCEQDLLWLPHYAQLQHAGRKR
                 1                                              45
B. subtilis Sfp  .MKIYGIYMDRPLSQEENEREMTFISPEKREKC....RRFYHKEDAHRTL B. brevis OrfX   ..........*IDRHVFNFLSSNVSKEKQQAFV....RYVNVKDAYRSL 50                                             89
E. coli EntD     KTEHLA.........GRIAAVYALREYGYKCVPAIGDVRQPVWPAEVYG
                 46                                             86
B. subtilis Sfp  LGDVLVRSVISRQYQLDKSDIRESTQEYGKPCIPDLPDAH.........E B. brevis OrfX   LGELLIRKYLIQVLNIPNENILERKNEYGKPFV.DF.DIH.........E 90                                             137
E. coli EntD     SISHCGTTALAVVSRQPIGIDIEEI..FSVQTARELTDNIITPAEHERLA
                 87                                             136
B. subtilis Sfp  NISHSGRWVIGAFDSQPIGIDIEKTKPISLEIAKREFSKTEYSDLLAKDK B. brevis OrfX   NISHSDEWVVCAISNHPVGIDIERISEIDIKIAEQFFHENEYIWLQSKAQ 138                                            187
E. coli EntD     DCGLAFSLALTLAFSAKESAFKASEIQTDAGFLDYQIISWNKQQVIIHRE
                 137                                            183
B. subtilis Sfp  DEQTDYEYHL...WSMKESFIKQEGKGLSLPLDSFSVRLHQDGQVSIELP B. brevis OrfX   NSQVSSEFEL...WTIKESYIKAIGKGMYIPINSFWIDKNQ.TQTVIYKQ 188                            209
E. coli EntD     N.................EMFAVHWQIKE.KIVITLCQHD
                 184                            225
B. subtilis Sfp  DSHSPCYIKTYEVDPGYKMAVCAAHPDFPE.DITMVSYEELL B. brevis OrfX   NKKEPVTIYEPELFEGYKCSCCSLFSSVTNLSITKLQVQELCNLFLDSTFSENNNF
```

BACILLUS SUBTILIS SIDEROPHORE GENES

This is a continuation-in-part of application Ser. No. 07/922,602 filed on Jul. 30, 1993 now abandoned.

Iron is essential to the growth of virtually all organisms. However, iron is not readily available in most biological systems. At neutral pH, iron forms insoluble salts,and in serum and secretory fluids, iron is tightly sequestered by host carrier proteins. Microorganisms have evolved various mechanisms of acquiring iron when confronted with iron-limiting conditions. Many microorganisms are capable of synthesizing and secreting siderophore molecules into the environment in response to iron deprivation. Siderophores bind to ferric ions with high affinity and are then reinternalized via specific receptor molecules found at the cell surface.

Figure 1A:
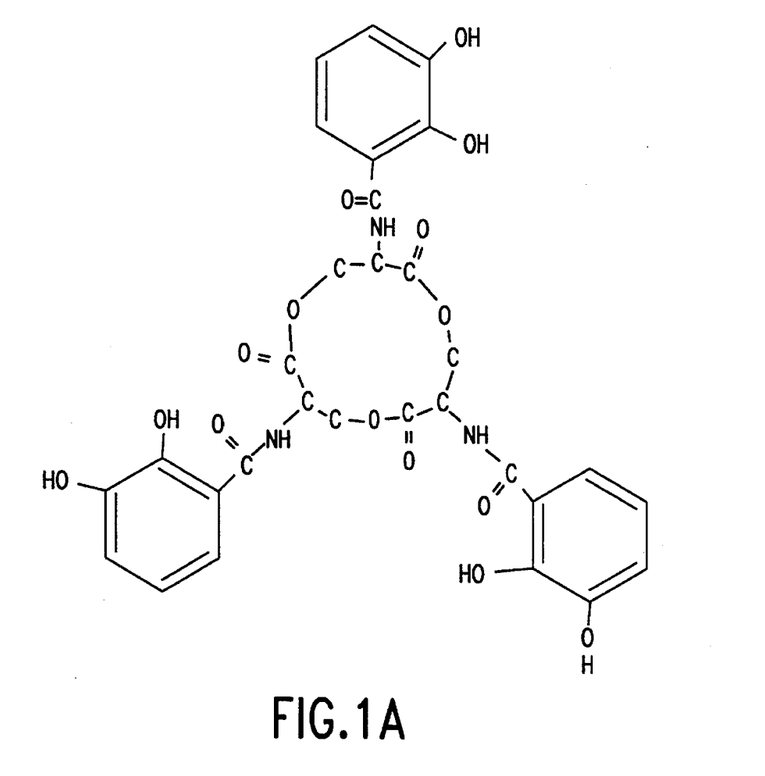
Figure 1B:
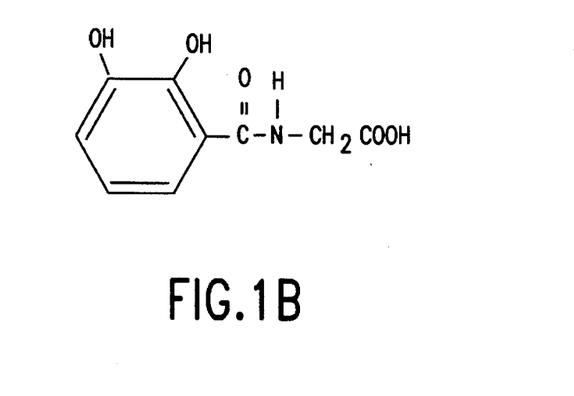
Figure 2:
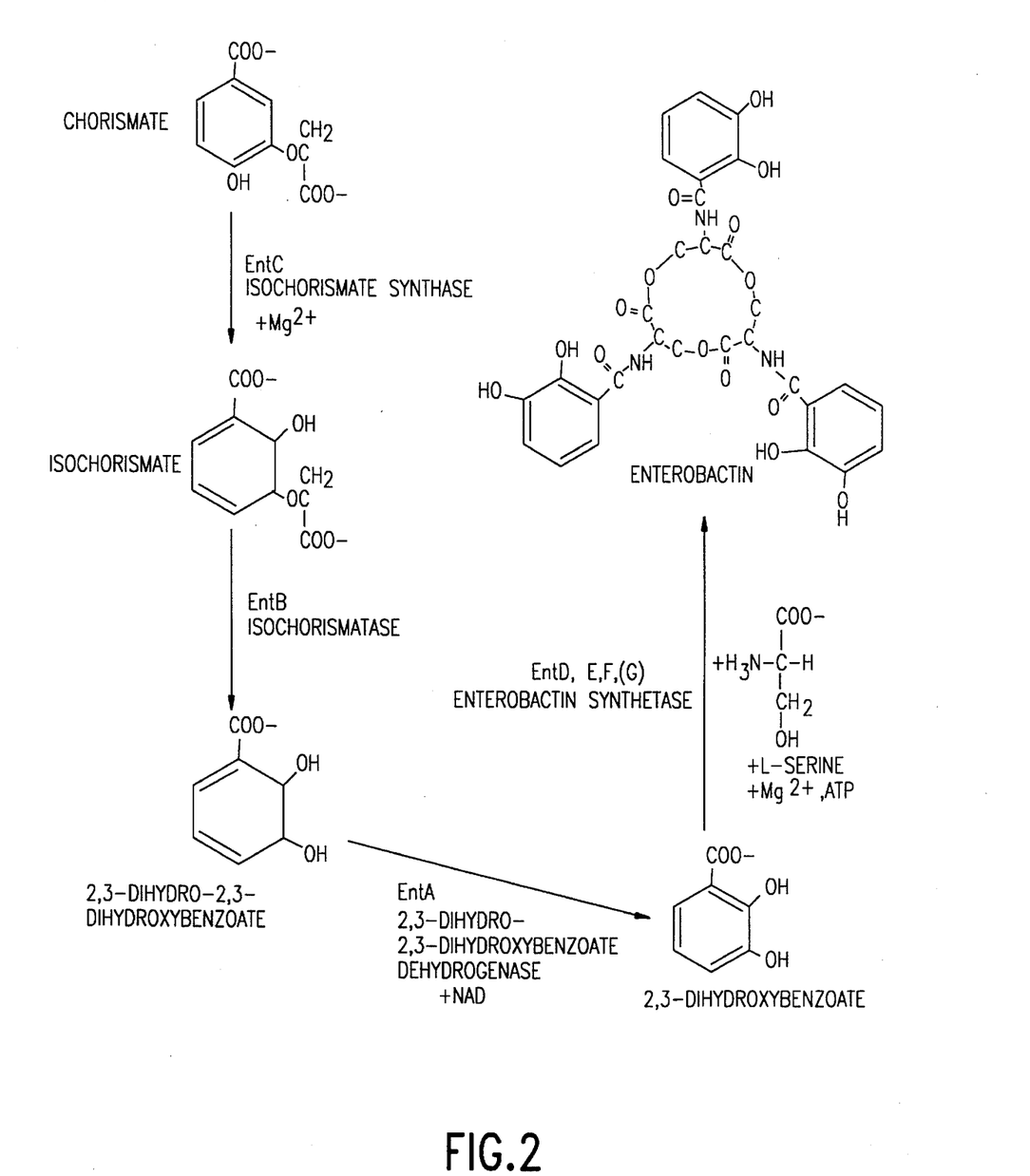
FIG. 2. The enterobactin biosynthetic pathway. Chorismate is enzymmatically converted to isochorismate by the product of the entC gene. The entB gene product then converts isochorismate to 2,3-dihydro-2,3-dihydroxybenzoate which is then converted, in an AND$^+$ dependent reaction, to 2,3-dihydroxybenzoate (DHB) by the entA gene product. The products of the entD, E, F and G genes form the enterobactin synthetase complex which catalyzes the last step of enterobactin synthesis. This final step requires serine, $Mg^{2+}$ and ATP.
Figure 3:
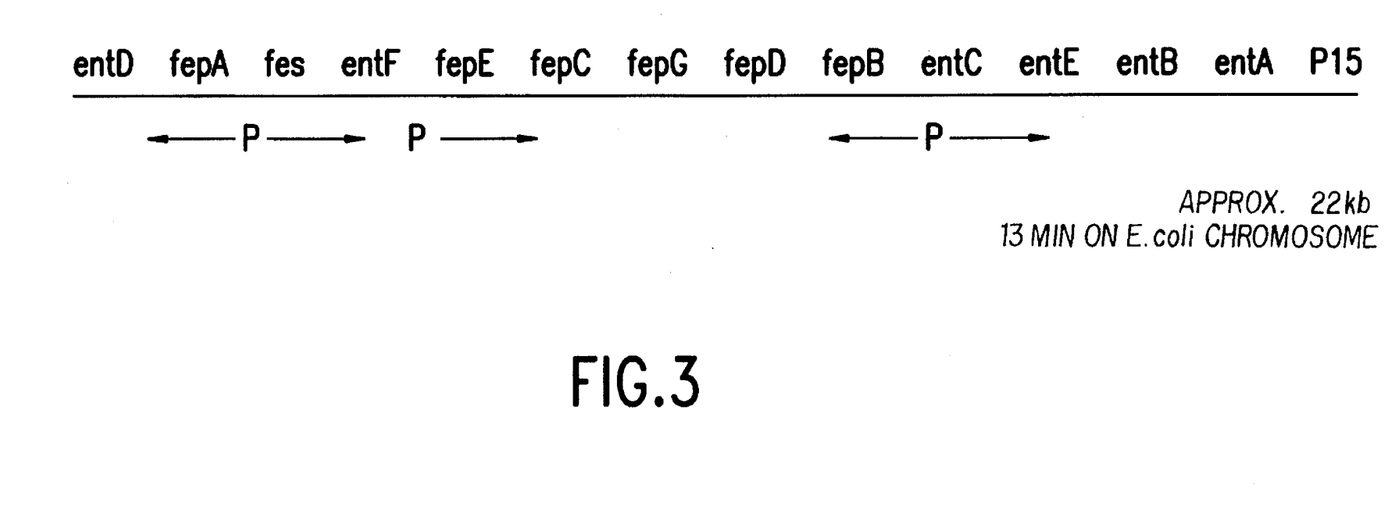
FIG. 3. Organization of the enterobactin genes in *E. coli*. The genes required for the biosynthesis and utilization of enterobactin are encoded in a 22 kilobase gene cluster located at minute 13 on the *E. coli* chromosome. The general location of the currently known promoters (P) and direction of transcription (arrows) are as indicated.

Much of what is known about iron transport in bacteria has been derived from studies with Gram-negative bacteria, especially *E. coli* (9). In contrast, much less is known about the mechanism(s) of iron acquisition of Gram-positive bacteria. In response to iron deprivation *E. coli* (Gram-negative) and *B. subtilis* (Gram-positive) both produce catecholic siderophores which are very similar in their structures (FIG. 1)(3,5) . *E. coli* produces the siderophore enterobactin (FIG. 1A). The products of the ent C, B and A genes enzlnnatically convert chorismate to dihydroxybenzoate (DHB) (FIG. 2). DHB is then converted to a cyclic trimer of 2,3-dihydroxybenzoyl serine (DHBS), enterobactin, by an enterobactin synthetase complex which is composed of the ent D, E, F and G gene products (8,11). At present, this last stage of enterobactin biosynthesis is poorly understood. The genes responsible for enterobactin biosynthesis and utilization are chromosomally encoded and clustered in several transcriptional units present on a 22 kilobase segment near minute 13 on the *E. coli* chromosome. These genes are coordinately regulated in response to the availability of iron.

From an antimicrobial standpoint, it stands to reason that the inhibition of iron acquisition would be at least bacteriostatic, if not eventually bactericidal. Devising strategies to inhibit the acquisition of iron by bacteria requires a good understanding of the mechanism(s) employed by the targeted bacteria. However, to date, this has been difficult to apply to Gram-positive organisms, the iron transport mechanisms of which are very poorly understood. *B. subtills* is known to secrete at least one siderophore, 2,3-dihydroxybenzoyl glycine (DHBG) (FIG. 1B) in response to iron stress (75); however, little else is known about the regulation, biosynthesis and utilization of siderophore in this or any other Gram-positive microorganism. The present invention provides the first insight into the genetic organization of the siderophore genes of a Gram-positive microorganism.

SUMMARY OF THE INVENTION

The present invention provides nucleic acid fragments comprising nucleic acid sequence encoding a Gram-positive siderophore. In a preferred embodiment, the gene is a Bacillus subtills gene. The *B. subtills* gene may encode EntA, EntB, EntC, EntD or EntE, or combinations thereof. The invention also provides recombinant vectors and host cells capable of expressing the siderophores.

Because the siderophores are essential to bacterial function under low iron conditions, the isolated fragments provide a useful tool in constructing microorganisms useful in a Gram-positive antibiotic screen. A host cell engineered to express only the Gram-positive siderophore function can be used to determine the effect of any given compound on the function of the siderophore. The inhibition or absence of growth of a transformed host cell in a low iron medium, when exposed to a particular compound, indicates the compound is a potential antibiotic candidate. The nucleic acid fragments are also useful as probes to identify homologous siderophore genes in other Gram-positive organisms such as pathogenic Staphylococcus aureus.

BRIEF DESCRIPTION OF THE FIGURES

FIG. 1. (A) *E. coli* enterobactin and (B) *B. subtills* 2,3-dihydroxybenzoyl glycine.

FIG. 8. Restriction map of plasmids pENTA4 and pENTA22. Linearized maps of pENT4 and pENT22 are presented. The *B. subtills* complementing activities associated with each plasmid is indicated. The white portion of the

DETAILED DESCRIPTION OF THE INVENTION

Initial endeavors to understand the mechanisms of *Bacillus subtills* iron acquisition focus on identifying, from a plasmid library containing *B. subtills* chromosomal DNA, clones capable of complementing *E. coli* ent mutants deficient in different enterobactin biosynthetic enzymes. Two sets of clones, containing approximately 5–10 Kb of *B. subtills* DNA with Ent$^+$ complementing activity are identified. One set contains clones which are all found to complement only an entD mutant. The second set contains clones that complement either entB mutants only, both entB and entE mutants, or entA, entB, entE and entC mutants. Restriction analysis indicates that the two sets of clones do not appear to be overlapping. The linkage of the EntC, EntE, EntB and EntA activities is in the same order as the corresponding genes in *E. coli*. The EntD activity genetically maps to a region near 199° on the *B. subtilis* chromosome. This data indicates that the siderophore biosynthetic genes of *E. coli* and *B. subtills* are functionally interchangeable, although the genetic organization of the genes is different.

Figure 5:
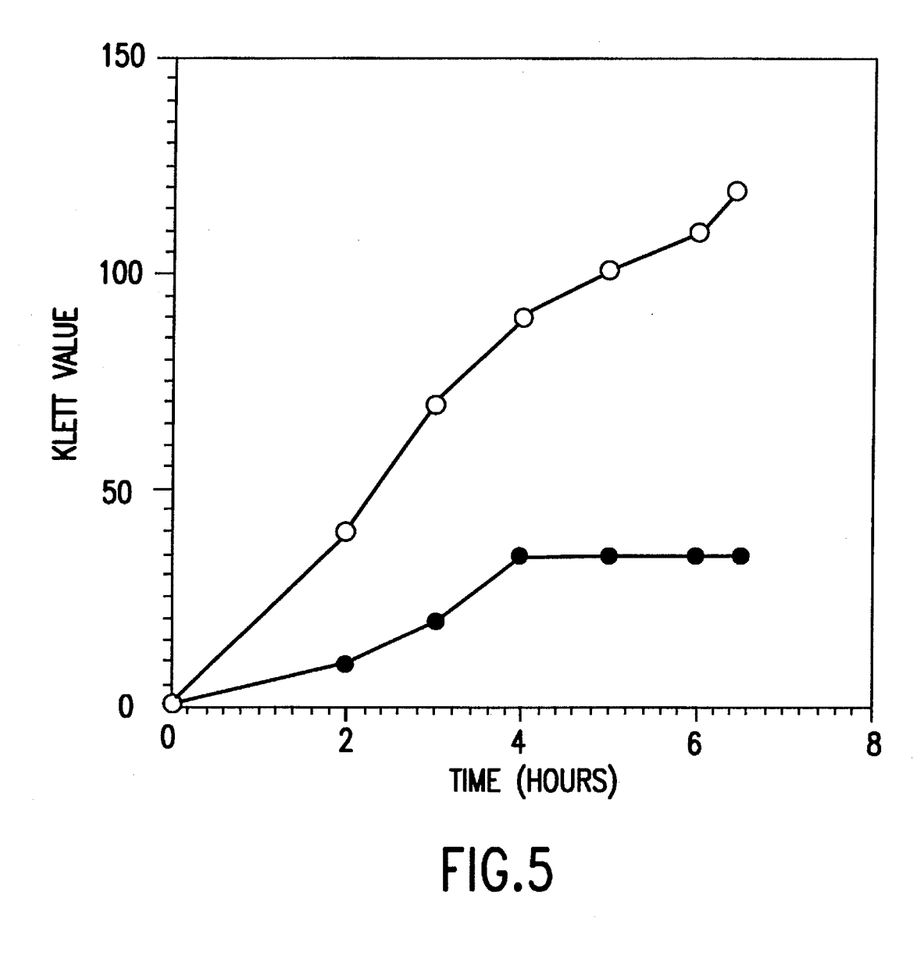
FIG. 5. Growth of the *B. subtills* Ent mutant in low iron medium. *B. subtills* strains are grown overnight at 37° C. in LB. The next day, cells are diluted into either LB or LB containing 120 μM ethylenediaminediacetic-acid EDDA (Klett value =10) and allowed to grow. (o), 168 grown in LB (□), 168 grown in LB EDDA; 168C grown in LB; and (■), 168C grown in LB EDDA.

To determine the roles of the Ent complementing activities in the native *B. subtills* host, an Ent$^-$ *B. subtills* mutant is created and its ability to grow in an iron poor medium is compared with a parent strain. Transposon mutagenesis is used to inactivate the EntD activities in plasmid pENTA22; inactivation is confirmed by the inability to complement *E. coli* entD mutants. The mutagenized plasmid is then used to construct a *B. subtilis* Ent$^-$ mutant by homologous recombination of the DNA encoding the interrupted genes into the chromosome. A transformant Ent$^-$ strain 168C is compared with a parent strain 16S for its ability to grow in iron poor medium. Although both strains grow equally well in iron rich medium, the growth curve of the parent strain shows that it is capable of continued growth in an iron depleted medium (FIG. 5), while the 168C strain ceases growth when the iron is depleted, reflecting its inability to produce siderophore. Similarly, spores of the parent strain are capable of germinating and growing to moderate density in the iron poor medium whereas the Ent$^-$ strain is unable to grow. These results support the conclusion that DHBG is a major high affinity iron transport system in *B. subtilis*, if not the only high affinity system. The nucleic acid fragment encoding the EntD activity clearly carries genetic information incorporated to the normal metabolic activity of *B. subtilis*.

Figure 6A:
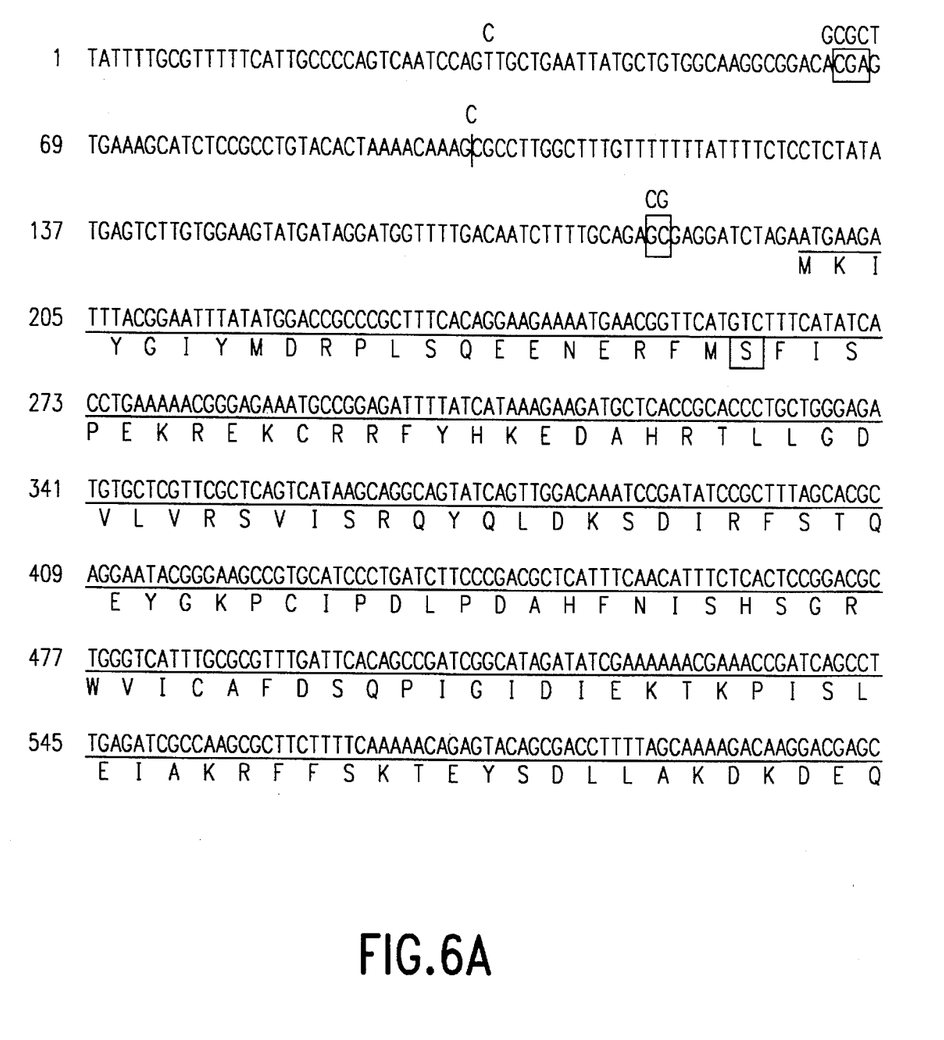
FIG. 6. Nucleotide sequence of pENTA22 sfp° gene. The predicted translated product is indicated below the underlined nucleotide sequence. Nucleotides in boxes indicate deviations from the published sequence for sfp° and the published sequence is either noted above the boxes, above individual nucleotides, or as insertions(l) and deletions (a) as indicated (7). The boxed serine residue at position 22 indicates a deviation from the published predicted amino acid sequence which placed a threonine residue at this position (7).
Figure 6B:
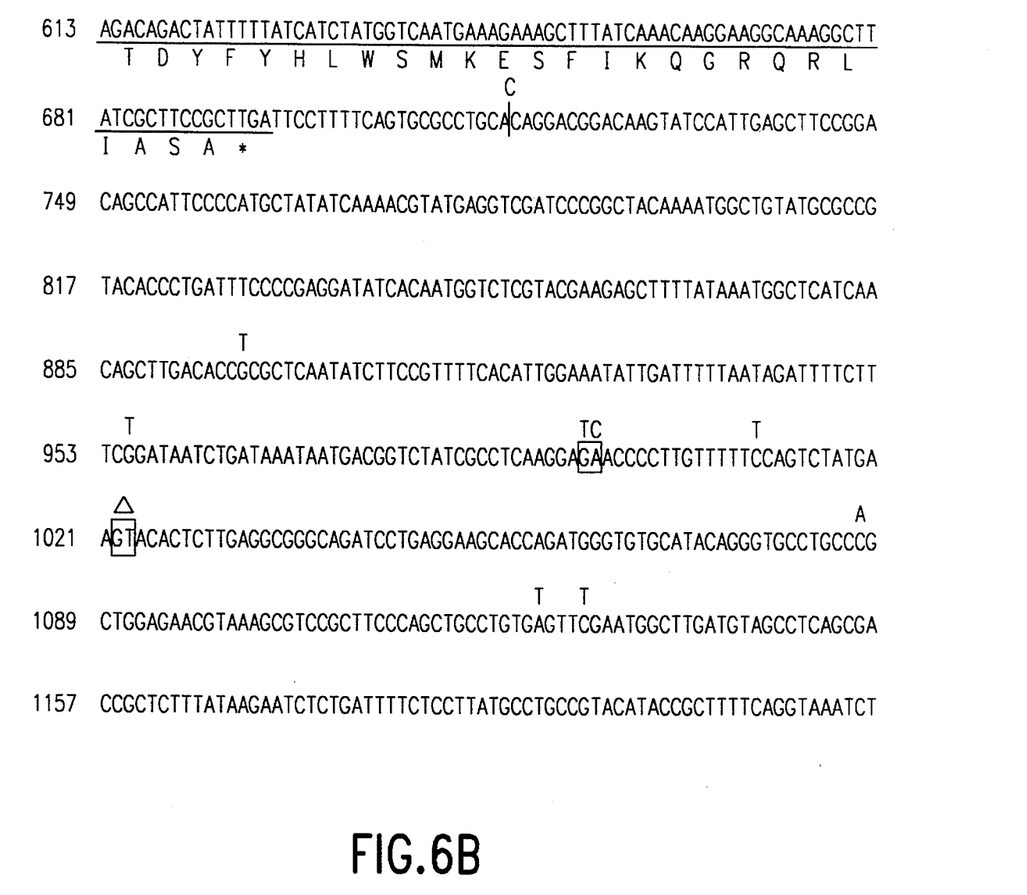
Figure 6C:
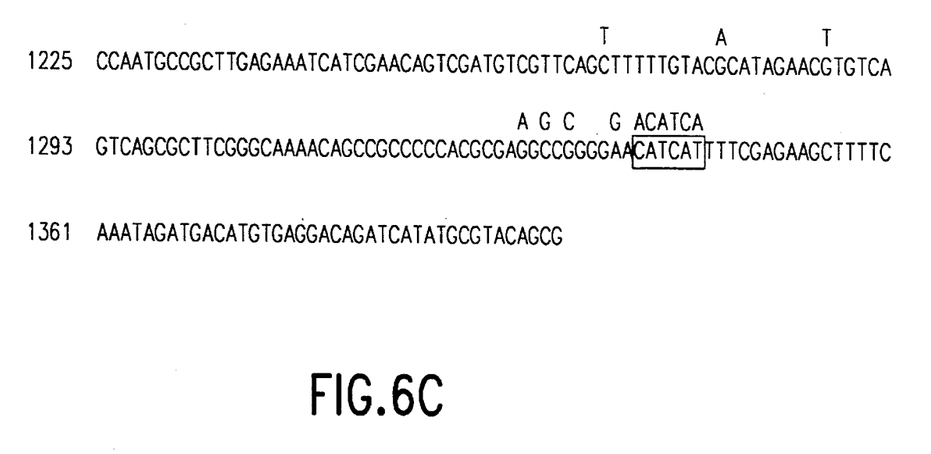

The nucleotide sequence of the *B. subtilis* DNA contained in plasmid pENTA22 is shown in FIG. 6. The entire sequence is analyzed for homologies to previously reported DNA and/or protein sequences using the Genetics Computer Group FASTA program.

An open reading frame, spanning base pairs 198 to 715 is sp°, a gene also described by Nakano et al. (7) and believed to be involved in the secretion of surfactin. The full-length sfp gene encodes a 224 amino acid polypeptide (7). The sfp gene is thought to encode a truncated 165 amino acid polypeptide with no known function, which differs from the homologous portion of the full-length sfp gene the five base pair substitutions and one base pair insertion (7). Upon comparison of the pentA22 sequence with the published sfp° sequence, differences in the flanking nucleotide sequence of the sfp° gene are observed, and a single difference within the coding region (FIG. 6). The inferred amino acid sequence of sfp° contains a threonine residue at position 22, while the corresponding residue in the pENTAa2-encoded sfp polypeptide is serine, a conservative difference which does not affect charge or polarity. Also confirmed is the location of the chromosomal insert in mutant 168C either within or just upstream of the sfp° gene.

Figure 7:
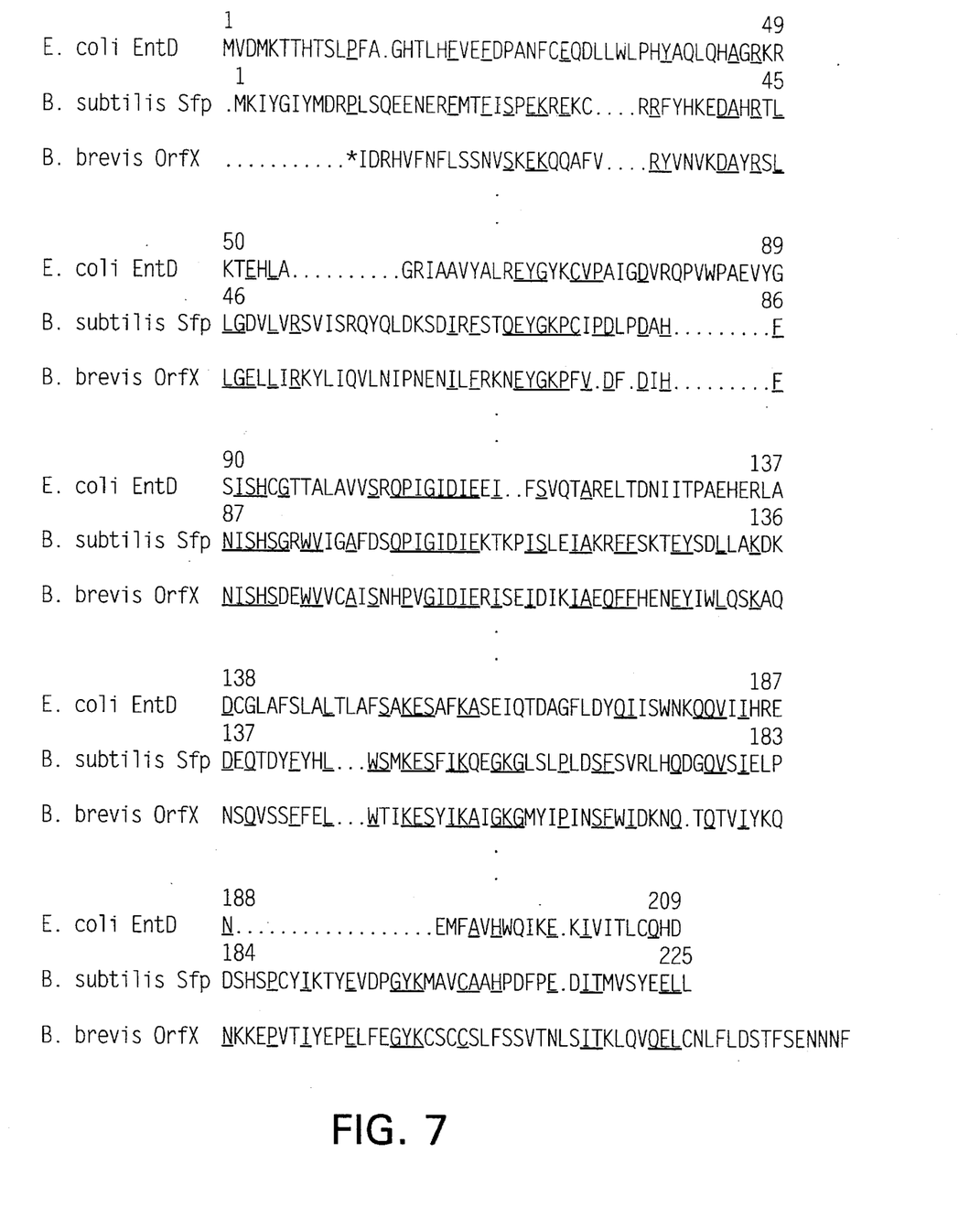
FIG. 7. A comparison of the predicted amino acid sequences of the *E. coli* entD gene, the *B. subtills* sfp gene, and the *B. brevis* grs orfX gene. The GCG GAP program is used to align two individual sequences at a time against each other. The best consensus alignment of all three sequences is done by hand. Underlined amino acid residues indicate identical residues conserved within at least two of the proteins. The asterisk (,) indicates the undetermined amino acid sequence of amino terminus of grs OrfX (4). Amino acid residues are numbered as indicated.
Figure 8:
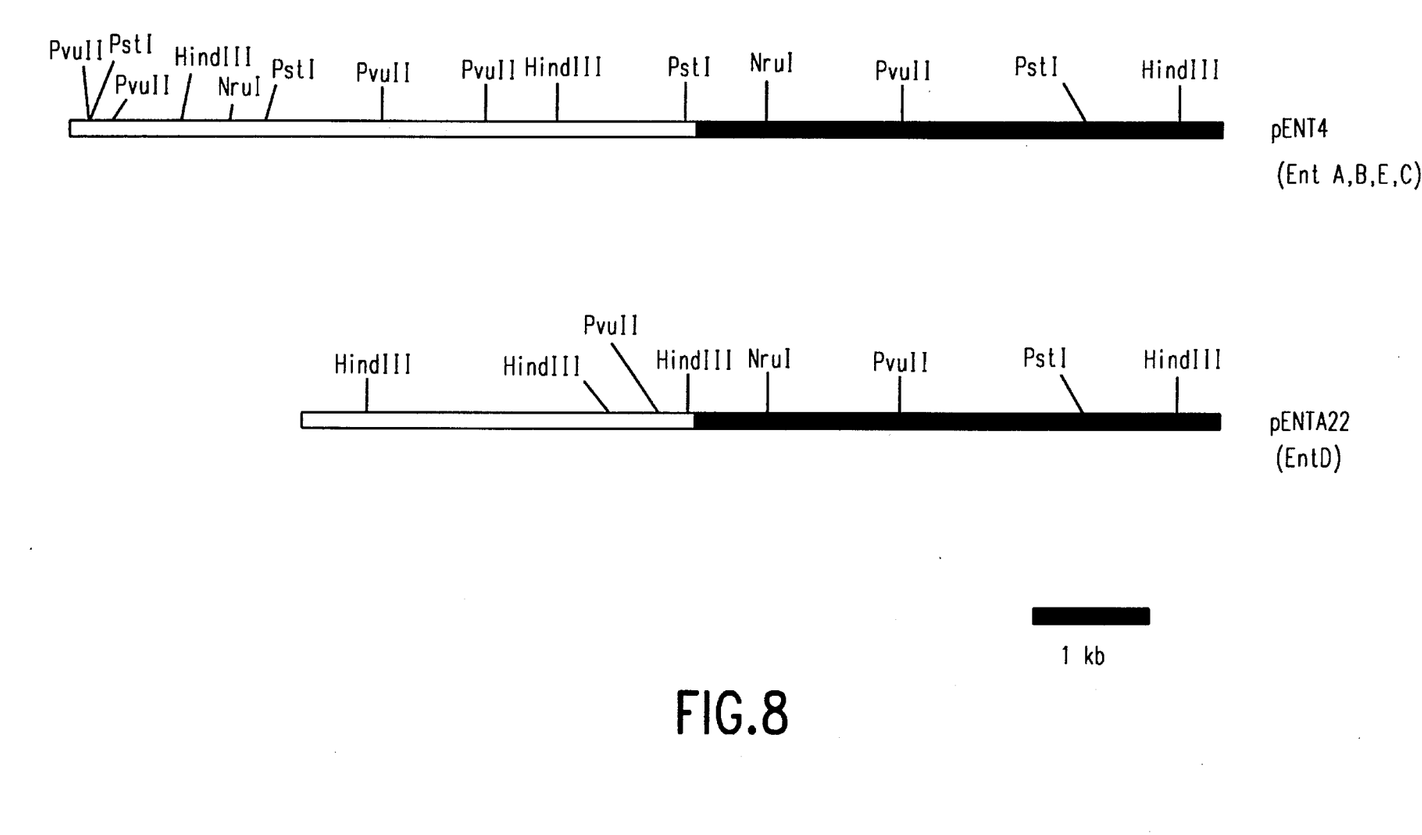

Using a data base search for proteins with sequence similarity to the inferred sfp gene product, Nakano and Zuber identified a homologous gene, orfX, an open reading frame in the *Bacillus brevis* gramicidin (grs) biosynthetic operon (4,6). Since the sfp° homologue on plasmid pENTA22 is originally identified by virtue of its ability to complement the defect in an *E. coli* entD mutant, a similar search of the database using the FASTA program, and looking for DNA and protein sequences with homology to sfp° and *E. coli* entD genes and polypeptides is performed. Other than orfX, no new homologous DNA sequences are identified. Using the GAP program, a comparison of the predicted amino acid sequences of sfp° and *E. coli* entD (1), and the partially sequenced *B. brevis* grs orfX (4) reveals identity between Sfp° and EntD, and 44% overall similarity. Sfp° and grs OrfX proteins are 38% identical and show an overall similarity of 57%. A comparison of EntD and grs OrfX reveal 21% identity and an overall similarity of 46%. Striking regions of identity common to all three proteins are observed (FIG. 7).

A GAP comparative search of *B. subtills* DNA sequence in plasmid pENTA22 is performed using the 14-base pair consensus sequence of the *E. coli* "Fur box" (2). The *E. coli* Fur box has been shown to bind the Fur repressor, a negative regulator which controls iron genes in response to iron-availability (3). A 37-base pair inverted repeat is identified lying downstream of ORF whose central portion exhibits identity with the *E. coli* Fur box, when aligned along the axis of symmetry. The function of this inverted repeat and the possibility of its iron-related role remains to be elucidated.

The availability of these nucleic acid fragments provides some basic tools for the study or iron transport in Gram-positive bacteria. For example, given the similarity between *E. coli* and *B. subtills* pathways, the metabolic pathways for iron transport in Gram-positive bacteria are also likely to be similar. It is therefore to be expected that the genes encoding these pathways will be similar from one Gram-positive microorganism to the next. Thus, the *B. subtills* nucleic acid fragments can be used as probes to detect the homologous genes in other Gram-positives, such as S. aureus, all methicillin resistant Staphylococci, vancomycin resistant enterococci, and other enterococci. In view of the broad utility of the specifically exemplified fragments, the invention therefore encompasses not only the *Bacillus subtilis* genes, but also those homologues in other species; i.e., other nucleic acid fragments encompassed are those which hybridize under medium or high stringency conditions with the exemplified *B. subtills* fragments, and which encode an *E. coli* complementing activity.

The invention, in addition to providing isolated nucleic acid fragments encoding Gram-positive siderophores, also provides vectors and host cells containing such fragments. The nucleic acid fragment can be used to express siderophore proteins in any appropriate eukaryotic or prokaryotic host cell line, using any expression vector suitable for the chosen cell line. Examples of suitable eukaryotic cells include mammalian cells, plant cells, yeast cells and insect cells. Suitable prokaryotic hosts, in addition to *B. subtills*, include *E. coli*. In a preferred embodiment, for ease of expression of the bacterial protein, the chosen host cell is prokaryotic.

Suitable expression vectors are selected based upon the choice of host cell. Numerous vectors suitable for use in transforming bacterial cells are well known. For example, plasmid and bacteriophages, such as A phage, are the most commonly used vectors for bacterial hosts, and for *E. coli* in particular. In both mammalian and insect cells, virus vectors are frequently used to obtain expression of exogenous DNA. In particular, mammalian cells are commonly transformed with SV40 or polyoma virus; and insect cells in culture may be transformed with baculovirus expression vectors. Yeast vector systems include yeast centromere plasmids, yeast episomal plasmids and yeast integrating plasmids. The invention encompasses any and all host cells transformed by the claimed genes, as well as expression vectors used to achieve this transformation.

A particularly useful function for the host cells and vectors of the present invention is in designing screens for novel antibiotic compounds. As shown above, the siderophore function is essential to the normal growth of *B. subtills* in low iron medium and, presumably, to other Gram-positive organisms. Thus, any substance which interferes with the iron transport function has potential Gram-positive antibiotic activity. To this end, novel microorganisms are created which express only the Gram-positive siderophore genes by transformation with the novel nucleic acid fragments. The starting microorganism should be one in which siderophore function has been eliminated, e.g., an Ent⁻ microorganism. In particular, for ease of manipulation and growth, *E. coli* is a particularly useful host cell. The host cell is then transformed with the Gram-positive siderophore gene.

Such recombinant microorganisms are then contacted with a putative antibiotic substance, or a mixture of substances such as a fermentation broth, and the effects of the substance on the growth of the microorganism in a low iron medium is observed. Such assays can be conducted as outlined below in the Examples. Any substance exhibiting inhibition of siderophore function represents a potential antibiotic candidate. This screening method is useful in detecting antibiotics having activity against any microorganism having an enterobactin-type siderophore mechanism, and in particular, Gram-positive microorganisms.

The invention is further illustrated in the following non-limiting examples.

EXAMPLES

Throughout the following examples, a number of vectors and cell lines are referred to. These are listed and their relevant properties summarized in Table 1.

TABLE 1

| Bacterial Strains, Plasmids and Bacteriophage | |
|---|---|
| Strain | Genotype or Phenotype |
| *E. coli* | |
| DH5α | endA1 gyrA96 hsdR17 supE44 thi-1 recA1 relA1 ΔlacU169 (φ80dlacZΔ(lacZ)M15) |
| AN193-60 | thi leuB proC trpE lacY mtl xyl rpsL azi thuA tsx supA ΔrecA entA |
| AN192-60 | like AN193-60, except entA⁺, entB |
| MT147 | like AN193-60, except entA⁺, entC::kan |
| AN90-60 | like AN193-60, except entA⁺, entD |

TABLE 1-continued

| Bacterial Strains, Plasmids and Bacteriophage | |
|---|---|
| Strain | Genotype or Phenotype |
| AN93-60 | like AN193-60, except entA⁺, entE |
| AN117-60 | like AN193-60, except entA⁺, entF |
| *B. subtilis* | |
| 168 | trpC2 |
| 168 trp⁺ | spontaneous trp⁺ revertant |
| 168Ctrp⁺ | chloramphenicol resistant, Ent⁻ |
| 1A10 | hisA1 thr-5, trpC2 |
| Plasmids | |
| pHP13 | chloramphenicol and erythromycin resistance |
| pENTA22 | contains *B. subtilis* entD complementing activity |
| pENTA22H | Same as pENTA22H1 except mini-kan Tn10 transposon interrupting entA and entD activities |
| pENTA22HC | Same as pENTA22H1 except chloramphenicol resistance gene from pHP13 inserted into kanamycin resistance gene |
| pENT4 | Contains *B. subtilis* entA, entB, entC, and entE homologues |
| Bacteriophage | |
| λ1105 | λ phage containing mini-kan Tn10 and Tn10 transposase under ptac control |

1. Isolation of *B. subtills* Library Clones

The American Cyanamid Company Medical Research Division *B. subtilis* library contains Sau3AI fragments of *B. subtilis* strain 168 chromosomal DNA cloned into the BamHI site of the tetracycline resistance gene of plasmid pBR322. The average insert size is 6.8 Kb. Library clones are selected by ampicillin resistance encoded by the intact β-lactamase gene on pBR322.

Ent⁻ *E. coli* strains are transformed with plasmids from the *B. subtills* library by electropotation, using a Biorad unit according to the manufacturer's instructions. Transformants are selected on chrome azurol S (CAS) agar plates (7) supplemented µg/ml ampicillin. CAS agar is characteristically blue when ferric iron is bound to CAS dye. When iron is chelated away from the CAS dye by a siderophore, the color changes from blue to orange. A colony which is actively secreting siderophore is readily identified by its surrounding orange halo. The *E. coli* ent⁻ mutants themselves cannot form orange halos on CAS agar; however, those ent⁻ cells which are transformed with a library clone that complements the ent⁻ mutation forms colonies surrounded by halos.

The transformation experiment identifies six independent library clones with ent⁻ complementing activity. These clones are characterized by restriction mapping and retransformed into all six *E. coli* ent⁻ mutants (Table 1) to determine which Ent activities they carry. The six library clones fall into two sets: one set contains EntD activities, and the other set contains either EntB alone, Ent B and EntE, or EntB, EntE, EntA and EntC activities.

2. Construction of a *B. subtills* Ent Mutant

Figure 4:
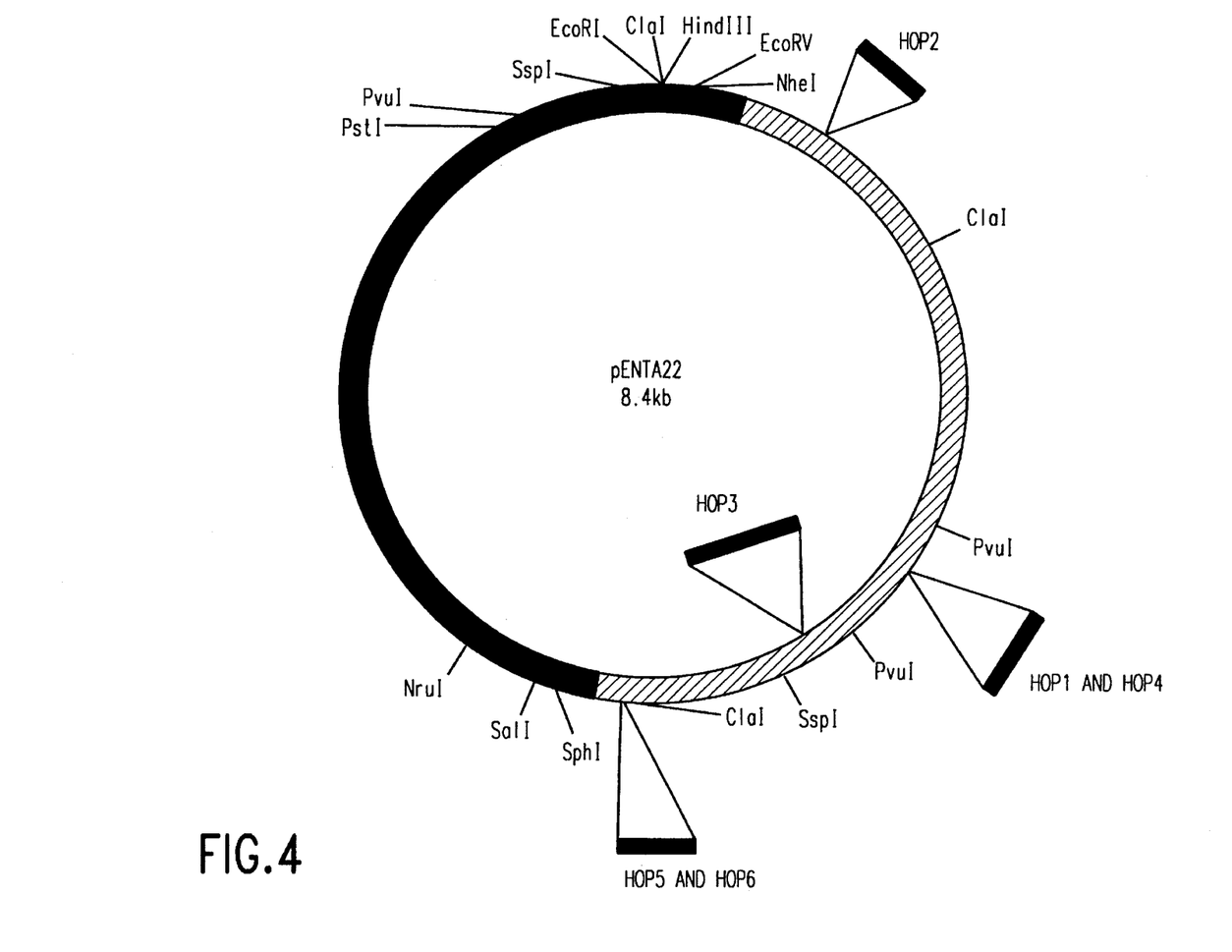
FIG. 4. Location of mini-kan Tn10 transpositions in pENTA22. A restriction map of pENTA22 is illustrated. The filled-in line of the plasmid represents pBR322 sequence and the stippled line of the plasmid represents *B. subtills* DNA. The general location of transposon insertions are as indicated and are labelled as "HOP".

As a first step in determining the role of the observed Ent complementary activity in the native host, an Ent⁻*B subtills* mutant is constructed. DH5α (pENTA22) cells are transfected with bacteriophage λ 1105 according to the method described by Way et al. (12). Transfected cells are spread into LB plates containing ampicillin, to select for the plasmid and Kanamycin to select for the transposon Tn 10. Ampicillin and kanamycin-resistant colonies are pooled and plasmid DNA isolated. The plasmid pool is then transformed into strain AN90-60. Transformants are selected on CAS agar containing ampicillin and kanamycin. Ampicillin and kanamycin resistant transformants which lack orange halos on CAS agar are examined by restriction enzyme analysis to confirm transposition events to the B. subtilis DNA insert of plasmid pENTA22. Six plasmids containing independent transposon hops are identified (FIG. 4). Two of the transposon hops (Hop1 and Hop4), which inactivate the EntD activities of pENTA22, are localized on the same 0.6 kilobase PvuI restriction fragment located within the B. subtills DNA of pENTAa2. One plasmid containing an inactivating insertion is chosen and named pENTA22H1. Plasmid pENTA22H1 fails to complement E. coli entD mutants as demonstrated by the fact that it no longer confers the ability to form orange halos on CAS agar. The remaining four hops retain EntD activities.

Because it no longer confers EntD activity in E. coli, plasmid of pENTA22H1 is selected to engineer a B. subtilis ent$^-$ mutant by homologous recombination of the interrupted gene into the chromosome. It is first necessary to engineer a selectable marker for B. subtills into the transposon of pENTA22H1. The chloramphenicol acetyl transferase gene (cat) from the shuttle plasmid HP13 is inserted into the unique xhoI site of pENTA22H1. Plasmid pHP13 DNA is digested with DraI and SmaI, in order to release the cat gene, and the DNA is reisolated. Plasmid pENTA22H1 DNA is digested with XhoI, the recessed ends are filled in with the Klenow fragment of DNA polymerase I, and the DNA is reisolated. Both digested plasmids are mixed together and ligated by standard methods and the ligated DNA is transformed into DH5α. Transformants are selected on LB plates containing ampicillin and chloramphenicol. Transformants are screened by restriction analysis and one clone with the expected restriction pattern, pENTA22HC1, is selected. This plasmid is transformed into B. subtills 168 by natural competence and fifteen chloramphenicol resistant mutants are isolated (at 5 µg/ml chloramphenicol). Since pENTA22HC1 cannot replicate in B. subtilis, any chloramphenicol resistant transformants contain the disrupted Ent activity integrated into the chromosome. Southern analysis confirms that one chloramphenicol resistant transformant, 168C, contains the cat gene inserted in the expected location in the cloned fragment.

3. Growth and Sporulation Properties of the B. subtills Ent$^-$ Mutant

To determine whether the EntD complementing activity plays a role in iron metabolism in B. subtilis, the ability of the B. subtilis Ent$^-$ mutant and parent strains to grow in iron-poor medium is measured. B. subtilis strains 168 and 168C are grown overnight at 37° C. in LB, washed in saline, and diluted into either LB (iron-rich) or LB containing 120 µM EDDA (iron-poor) and allowed to grow. Growth is estimated by culture optical density at 600 nm, or by means of a Klett-Summerson colorimeter (green filter). Both strains grow equally well in LB medium. The growth curve of the parent strain, 168, in Chelex LB is diauxic (FIG. 5), reflecting the ability of the parent strain to produce siderophore once the growth medium becomes iron depleted. In contrast, the Ent mutant, 168C, does not grow any further after iron depletion of the medium, reflecting its inability to produce siderophore. In addition, sporulation is determined following growth in DSM medium (8). Spores of the parent strain are able to germinate and grow to moderate density in LB containing 120 µM EDDA, whereas spores of the mutant strain are unable to grow (Table 2).

TABLE 2

| Growth$^a$ of 168 and 168C in Low-Iron Medium | | |
|---|---|---|
| Strain | LB | LB + 120 µM EDDA |
| 168 | 1.783 | 0.499 |
| 168C | 1772 | 0.055 |

Note:
$^a$Medium is inoculated with $10^6$ spores and cultures are grown overnight at 37° C. Growth is determined by measuring the O.D. of the culture at 600 nm following 24 hours of growth.

4. Genetic Mapping of B. subtills EntD Activity

Because it contains a convenient antibiotic resistance marker linked to EntD activity, B. subtilis 168C trp$^+$ is used to map the location of this Ent activity in the B. subtilis chromosome. Mapping is done by both PBS1 transduction and transformation. PBS1 transduction is according to the method of Takahashi (10), except that the recipient cells are grown in Brain Heart Infusion media (Difco). PBS1 lysates are made using Tn 917 mapping kit strains obtained from Bacillus Genetic Stock Center. Each lysate is used to transduce 168Ctrp$^+$, selecting for erythromycin and lincomycin-resistant transductants. Transductants are screened for sensitivity to chloramphenicol. Linkage to a given TN 917 insertion is determined by dividing the number of erythromycin and lincomycin resistant and chloramphenicol sensitive transductants by the total number of erythromycin resistant transductants. By transformation, EntD shows 6–18% linkage to trpC2, near 199° in the B. subtilis chromosome. This differs from the reported locations of sfp at 40° (8).

5. Nucleotide Sequence

Determination and Analysis

The B. subtilis DNA contained in plasmid pENTA22 is sequenced using the sequenase Version 2.0 kit (U.S. Biochemicals) according to the manufacturer's recommendations. The template is denatured doublestranded DNA. Unidirectional exonuclease III deletions of plamsid pENTA22 are generated using the Promega Erase-a-Base system. All primers are synthesized in-house. Both strands of pENTA22 are sequenced to ensure accuracy. Nucleotide sequence compilation, analysis and comparative searches are done using the Genetics Computer Group (1992, Version 7.2, Madison Wisconsin) SEQED, MAP, GAP and FASTA programs and Genbank and Swissprot data bases. The sequence is depicted in FIG. 7.

DEPOSIT OF BIOLOGICAL MATERIALS

The following biological materials have been deposited with the American Type Culture Collection, 12301 Parklawn Drive, Rockville, Md., under the Budapest Treaty, and given the indicated Accession Numbers:

| Description | Accession No. |
|---|---|
| E. coli DH5α (pENTA1) | ATCC 68985 |
| E. coli DH5α (pENTB2) | ATCC 68986 |
| E. coli DH5α (pENT4) | ATCC 69284 |

REFERENCES

1. Ames, G. F. L., S. S. Mimura and V. Shyamala, TEMS Microbiol. Rev. 75:429–446, 1990.

2. DeLorenzo, V., S. Wee, M. Herrero, J. B. Neilands, J. Bacteriol., 169:2624–2630, 1987.

3. Earhart, C. F., in G. Winkelmann, D. van der Helm, J. B. Neilands (eds.), Iron Transport in Microbes, Plants and Animals. VCH Verlagsgesellschaft mbH, Weinheim, FRG, pp. 67–81, 1987.

4. Greenwood, K. T. and R. K. J. Luke, Biochem. Biophys. Acta., 614:185–195.

5. Ito, T. and J. B. Neilands, J. Am. Chem. Soc., 80:4645–4647, 1958.

6. Miller, J. H., Experiments in Molecular Genetics. Cold Spring Harbor Laboratory, 1972.

7. Nakano, M. M., M. A. Marahiel and P. Zuber, Mol. Gen. Genet., 232:313–321, 1992.

8. Nakano, M. M., R. Magnuson, A. Myers, J. Curry, A. D. Grossman and P. Zuber, J. Bacteriol., 173:1170–1178, 1991.

9. Staab, J. F. and C. F. Earhart, J. Bacteriol., 172:6403–6410, 1990.

10. Takahashi, I., J. Gen. Microbiol., 31:211–217, 1963.

11. Walker, J. E., M. Saraste, M. J. Runswick, N. J. Gay, EMBO J, 1:945–957, 1982.

12. Way, J. C., M. A. Davis, D. Morisato, D. E. Roberts and N. Kleckner, Gene, 32:369–379, 1984.

What we claim is:

1. A method for identifying compounds having potential antibiotic activity against microorganisms with an enterobactin-type siderophore comprising contacting a host cell transformed with an isolated nucleic acid sequence comprising nucleotides 198 to 715 of SEQ ID NO:1, or an isolated nucleic acid sequence contained in plasmid pENTA1, pENT4, or pENTB2 with the compound to be tested, and observing the presence or absence of an effect of the compound on the host cell's ability to grow in low iron medium, wherein compounds that inhibit the host cell's ability to grow in low iron medium are identified as compounds with potential antibiotic activity.

2. A host cell transformed with a vector comprising a plasmid selected from the group consisting of pENTA1, pENT4, and pENTB2.

3. The host cell of claim 2 which is a prokaryotic cell.

4. The host cell of claim 3 which is a bacterium.

5. The host cell of claim 4 which is E. coli.

6. The host cell of claim 3 which is E. coli.

7. A vector comprising plasmid pENTA1.

8. A vector comprising plasmid pENT4.

9. A vector comprising plasmid pENTB2.

10. Plasmid pENTA1 deposited under ATCC accession number 68985.

11. Plasmid pENT4 deposited under ATCC accession number 69284.

12. Plasmid pENTB2 deposited under ATCC accession number 68986.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1400 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( v i ) ORIGINAL SOURCE:
        ( A ) ORGANISM: Bacillus subtilis     ( i x ) FEATURE:
        ( A ) NAME/KEY: CDS
        ( B ) LOCATION: 198..697

( x i ) SEQUENCE DESCRIPTION: SEQ ID NO:1:

```
TATTTTGCGT  TTTTCATTGC  CCCAGTCAAT  CCAGTTGCTG  AATTATGCTG  TGGCAAGGCG              60

GACACGAGTG  AAAGCATCTC  CGCCTGTACA  CTAAACAAA   GCGCCTTGGC  TTTGTTTTTT             120

TATTTTCTCC  TCTATATGAG  TCTTGTGGAA  GTATGATAGG  ATGGTTTTGA  CAATCTTTTG             180

CAGAGCGAGG  ATCTAGA ATG  AAG  ATT  TAC  GGA  ATT  TAT  ATG  GAC  CGC  CCG           230
                    Met  Lys  Ile  Tyr  Gly  Ile  Tyr  Met  Asp  Arg  Pro
                      1                 5                         10

CTT  TCA  CAG  GAA  GAA  AAT  GAA  CGG  TTC  ATG  TCT  TTC  ATA  TCA  CCT  GAA     278
Leu  Ser  Gln  Glu  Glu  Asn  Glu  Arg  Phe  Met  Ser  Phe  Ile  Ser  Pro  Glu
              15                      20                      25

AAA  CGG  GAG  AAA  TGC  CGG  AGA  TTT  TAT  CAT  AAA  GAA  GAT  GCT  CAC  CGC     326
Lys  Arg  Glu  Lys  Cys  Arg  Arg  Phe  Tyr  His  Lys  Glu  Asp  Ala  His  Arg
         30                      35                      40

ACC  CTG  CTG  GGA  GAT  GTG  CTC  GTT  CGC  TCA  GTC  ATA  AGC  AGG  CAG  TAT     374
Thr  Leu  Leu  Gly  Asp  Val  Leu  Val  Arg  Ser  Val  Ile  Ser  Arg  Gln  Tyr
     45                      50                      55

CAG  TTG  GAC  AAA  TCC  GAT  ATC  CGC  TTT  AGC  ACG  CAG  GAA  TAC  GGG  AAG     422
Gln  Leu  Asp  Lys  Ser  Asp  Ile  Arg  Phe  Ser  Thr  Gln  Glu  Tyr  Gly  Lys
```

| | | | | | | | | | | | | | | | |
|---|---|---|---|---|---|---|---|---|---|---|---|---|---|---|---|
| CCG | TGC | ATC | CCT | GAT | CTT | CCC | GAC | GCT | CAT | TTC | AAC | ATT | TCT | CAC | TCC | 470
| Pro | Cys | Ile | Pro | Asp | Leu | Pro | Asp | Ala | His | Phe | Asn | Ile | Ser | His | Ser |
| | | | 80 | | | | | 85 | | | | | | 90 | |

```
CCG TGC ATC CCT GAT CTT CCC GAC GCT CAT TTC AAC ATT TCT CAC TCC    470
Pro Cys Ile Pro Asp Leu Pro Asp Ala His Phe Asn Ile Ser His Ser
            80              85                      90

GGA CGC TGG GTC ATT TGC GCG TTT GAT TCA CAG CCG ATC GGC ATA GAT    518
Gly Arg Trp Val Ile Cys Ala Phe Asp Ser Gln Pro Ile Gly Ile Asp
            95              100                     105

ATC GAA AAA ACG AAA CCG ATC AGC CTT GAG ATC GCC AAG CGC TTC TTT    566
Ile Glu Lys Thr Lys Pro Ile Ser Leu Glu Ile Ala Lys Arg Phe Phe
        110             115                 120

TCA AAA ACA GAG TAC AGC GAC CTT TTA GCA AAA GAC AAG GAC GAG CAG    614
Ser Lys Thr Glu Tyr Ser Asp Leu Leu Ala Lys Asp Lys Asp Glu Gln
        125             130                 135

ACA GAC TAT TTT TAT CAT CTA TGG TCA ATG AAA GAA AGC TTT ATC AAA    662
Thr Asp Tyr Phe Tyr His Leu Trp Ser Met Lys Glu Ser Phe Ile Lys
140             145                 150                     155

CAA GGA AGG CAA AGG CTT ATC GCT TCC GCT TGA TT  CCTTTTCAGT         707
Gln Gly Arg Gln Arg Leu Ile Ala Ser Ala  *
                160             165

GCGCCTGCAC AGGACGGACA AGTATCCATT GAGCTTCCGG ACAGCCATTC CCCATGCTAT  767
ATCAAAACGT ATGAGGTCGA TCCCGGCTAC AAAATGGCTG TATGCGCCGT ACACCCTGAT  827
TTCCCCGAGG ATATCACAAT GGTCTCGTAC GAAGAGCTTT TATAAATGGC TCATCAACAG  887
CTTGACACCG CGCTCAATAT CTTCCGTTTT CACATTGGAA ATATTGATTT TAATAGATT   947
TTCTTTCGGA TAATCTGATA AATAATGACG GTCTATCGCC TCAAGGAGAA CCCCTTGTTT 1007
TTCCAGTCTA TGAAGTACAC TCTTGAGGCG GGCAGATCCT GAGGAAGCAC CAGATGGGTG 1067
TGCATACAGG GTGCCTGCCC GCTGGAGAAC GTAAAGCGTC CGCTTCCCAG CTGCCTGTGA 1127
GTTCGAATGG CTTGATGTAG CCTCAGCGAC CGCTCTTTAT AAGAATCTCT GATTTTCTCC 1187
TTATGCCTGC CGTACATACC GCTTTTCAGG TAAATCTCCA ATGCCGCTTG AGAAATCATC 1247
GAACAGTCGA TGTCGTTCAG CTTTTTGTAC GCATAGAACG TGTCAGTCAG CGCTTCGGGC 1307
AAAACAGCCG CCCCCACGCG AGGCCGGGGA ACATCATTTT CGAGAAGCTT TTCAAATAGA 1367
TGACATGTGA GGACAGATCA TATGCGTACA GCG                              1400
```

( 2 ) INFORMATION FOR SEQ ID NO:2:

( i ) SEQUENCE CHARACTERISTICS:
            ( A ) LENGTH: 165 amino acids
            ( B ) TYPE: amino acid
            ( D ) TOPOLOGY: linear         ( i i ) MOLECULE TYPE: protein         ( x i ) SEQUENCE DESCRIPTION: SEQ ID NO:2:

```
Met Lys Ile Tyr Gly Ile Tyr Met Asp Arg Pro Leu Ser Gln Glu Glu
 1               5                  10                  15

Asn Glu Arg Phe Met Ser Phe Ile Ser Pro Glu Lys Arg Glu Lys Cys
                20                  25                  30

Arg Arg Phe Tyr His Lys Glu Asp Ala His Arg Thr Leu Leu Gly Asp
            35                  40                  45

Val Leu Val Arg Ser Val Ile Ser Arg Gln Tyr Gln Leu Asp Lys Ser
        50                  55                  60

Asp Ile Arg Phe Ser Thr Gln Glu Tyr Gly Lys Pro Cys Ile Pro Asp
 65                  70                  75                  80

Leu Pro Asp Ala His Phe Asn Ile Ser His Ser Gly Arg Trp Val Ile
                85                  90                  95
```

-continued

| Cys | Ala | Phe | Asp 100 | Ser | Gln | Pro | Ile | Gly 105 | Ile | Asp | Ile | Glu | Lys 110 | Thr | Lys |
| Pro | Ile | Ser 115 | Leu | Glu | Ile | Ala | Lys 120 | Arg | Phe | Phe | Ser | Lys 125 | Thr | Glu | Tyr |
| Ser | Asp 130 | Leu | Leu | Ala | Lys | Asp 135 | Lys | Asp | Glu | Gln | Thr 140 | Asp | Tyr | Phe | Tyr |
| His 145 | Leu | Trp | Ser | Met | Lys 150 | Glu | Ser | Phe | Ile | Lys 155 | Gln | Gly | Arg | Gln | Arg 160 |
| Leu | Ile | Ala | Ser | Ala 165 | | | | | | | | | | | |